(12) United States Patent
Lin et al.

(10) Patent No.: US 8,312,395 B2
(45) Date of Patent: Nov. 13, 2012

(54) AUTOMATIC IDENTIFICATION OF SYSTEMATIC REPEATING DEFECTS IN SEMICONDUCTOR PRODUCTION

(75) Inventors: Paul Kuang Chi Lin, Shanghai (CN); Dong Kang, Shanghai (CN); Yong Gang Wang, Shanghai (CN); Yulei Zhang, Shanghai (CN)

(73) Assignee: Semiconductor Manufacturing International (Shanghai) Corporation, Shanghai (CN)

( * ) Notice: Subject to any disclaimer, the term of this patent is extended or adjusted under 35 U.S.C. 154(b) by 1 day.

(21) Appl. No.: 13/007,556

(22) Filed: Jan. 14, 2011

(65) Prior Publication Data

US 2012/0023464 A1 Jan. 26, 2012

(30) Foreign Application Priority Data

Jan. 15, 2010 (CN) .......................... 2010 1 0022874

(51) Int. Cl.
*G06F 17/50* (2006.01)
(52) U.S. Cl. .......................................... 716/52; 716/54
(58) Field of Classification Search .................. 716/54, 716/52
See application file for complete search history.

(56) References Cited

U.S. PATENT DOCUMENTS

| 5,240,866 A | 8/1993 | Friedman et al. |
| 5,544,256 A | 8/1996 | Brecher et al. |
| 5,665,609 A | 9/1997 | Mori |
| 5,991,699 A | 11/1999 | Kulkarni et al. |
| 7,730,434 B2 * | 6/2010 | Aghababazadeh et al. ... 716/136 |
| 2008/0081385 A1* | 4/2008 | Marella et al. .................. 438/14 |
| 2008/0315196 A1* | 12/2008 | Aghababazadeh et al. ..... 257/48 |
| 2009/0297019 A1* | 12/2009 | Zafar et al. .................... 382/145 |
| 2010/0119144 A1* | 5/2010 | Kulkarni et al. .............. 382/149 |
| 2011/0286656 A1* | 11/2011 | Kulkarni et al. .............. 382/144 |

FOREIGN PATENT DOCUMENTS

CN 101210932 A 2/2008

* cited by examiner

*Primary Examiner* — Suresh Memula
(74) *Attorney, Agent, or Firm* — Kilpatrick Townsend & Stockton LLP

(57) ABSTRACT

A method includes capturing an image of the pattern using one or more scans across a surface of the partially completed wafer. The method includes processing information associated with the captured image of the pattern in a first format (e.g., pixel domain) into a second format, e.g., transform domain. The method includes determining defect information associated with the image of the pattern in the second format and processing the defect information (e.g., wafer identification, product identification, layer information, x-y die scanned) to identify at least one defect associated with a spatial location of a repeating pattern on the partially completed wafer provided by a reticle. The method includes identifying the reticle associated with the defect and a stepper associated with the reticle having the defect and ceasing operation of the stepper. The damaged reticle is replaced, and the process resumes using a replaced reticle.

20 Claims, 8 Drawing Sheets

AUTOMATIC IDENTIFICATION OF SYSTEMATIC REPEATING DEFECTS IN SEMICONDUCTOR PRODUCTION

CROSS-REFERENCE TO RELATED APPLICATIONS

This present application claims priority to Chinese Patent Application No. 201010022874.9, filed on Jan. 15, 2010, which is commonly owned and incorporated by reference herein for all purposes.

BACKGROUND OF THE INVENTION

Embodiments of the present invention generally relate to integrated circuits and the processing for the manufacture of semiconductor devices. In particular, embodiments of the invention provide a method and system for performing patterning processes for the manufacture of integrated circuit devices. More particularly, embodiments of the present method provide an image capturing and processing technique for identifying repeating pattern defects in a retical mask used for the manufacture of integrated circuits. But it would be recognized that the invention has a much broader range of applicability. As merely an example, the method and system can be applied to other devices such as micro electrical mechanical systems, display devices, and others.

Integrated circuits have evolved from a handful of interconnected devices fabricated on a single chip of silicon to millions of devices. Conventional integrated circuits provide performance and complexity far beyond what was originally imagined. In order to achieve improvements in complexity and circuit density (i.e., the number of devices capable of being packed onto a given chip area), the size of the smallest device feature, also known as the device "geometry", has become smaller with each generation of integrated circuits.

Increasing circuit density has not only improved the complexity and performance of integrated circuits but has also provided lower cost parts to the consumer. An integrated circuit or chip fabrication facility can cost hundreds of millions, or even billions, of U.S. dollars. Each fabrication facility will have a certain throughput of wafers, and each wafer will have a certain number of integrated circuits on it. Therefore, by making the individual devices of an integrated circuit smaller, more devices may be fabricated on each wafer, thus increasing the output of the fabrication facility. Making devices smaller is very challenging, as each process used in integrated fabrication has a limit. That is to say, a given process typically only works down to a certain feature size, and then either the process or the device layout needs to be changed. Additionally, as devices require faster and faster designs, process limitations exist with certain conventional processes and materials.

An example of a process that has limitations based upon a given feature size is lithographic techniques for MOS transistor devices. As merely an example, lithography has been a major limitation as device sizes continue to become smaller. A major issue is repeating defects that occur in the manufacture of integrated circuits. These repeating defects are often difficult to determine and often cause high yield losses when they are undetected. These and other limitations associated with conventional lithography processes can be found throughout the present specification and more particularly below.

From the above, it is seen that an improved technique for processing semiconductor devices is desired.

BRIEF SUMMARY OF THE INVENTION

Embodiments of the present invention provide techniques for processing integrated circuits for the manufacture of semiconductor devices. In particular, embodiments of the invention provide a method and system for performing patterning processes for the manufacture of integrated circuit devices. More particularly, the present method provides an image capturing and processing technique for identifying repeating pattern defects in a retical mask used for the manufacture of integrated circuits. But it would be recognized that the invention has a much broader range of applicability. As merely an example, the method and system can be applied to other devices such as micro electrical mechanical systems, display devices, and others.

A specific embodiment of the present invention provides a method for processing an integrated circuit device, e.g., memory, application specific integrated circuits, micros, and others. The method includes providing a partially completed semiconductor wafer, which has one or more patterns, e.g., etched. The method includes capturing an image of the pattern using one or more scans across a surface of the partially completed wafer. In a specific embodiment, the method uses an imaging device such as a digital camera, or the likes. The method includes processing information associated with the image of the pattern in a first format (e.g., pixel domain) into a second format, e.g., transform domain. The method includes determining defect information associated with the image of the pattern in the second format. The method includes processing the defect information (e.g., wafer identification, product identification, layer information, x-y die scanned) of the partially completed wafer to identify at least one defect associated with a spatial location of a repeating pattern on the partially completed wafer provided by a reticle. The method also identifies the reticle associated with the defect and a stepper associated with the reticle having the defect; and ceasing operation of the stepper. In a preferred embodiment, the stepper with a damaged reticle is ceased before damaging other in-process wafers. The damaged reticle is replaced, and the process resumes using a replaced reticle, which is free from defects according to a specific embodiment.

In an alternative specific embodiment, the invention provides a system for processing an integrated circuit device, which has one or more memories, e.g., fixed, solid state. The one or more memories include various computer codes. These codes include one or more codes directed to processing defect information of a partially completed wafer; and one or more codes directed to identify at least one defect associated with a spatial location of a repeating pattern on the partially completed wafer provided by a reticle. Depending upon the embodiment, there can be other computer codes that carry out the functionality described herein as well as outside of the present specification.

Embodiments of the present invention provide many benefits over conventional techniques. For example, embodiments of the present technique provide an easy to use process that relies upon conventional technology. In some embodiments, the method provides higher device yields in dies per wafer. Additionally, the method provides a process that is compatible with conventional process technology without substantial modifications to conventional equipment and processes. Preferably, the invention provides for an improved technique to identify a repeating defect in a reticle device, which is then identified. A stepper system using the identified reticle is stopped to prevent further damage to in-process wafers. Depending upon the embodiment, one or more of these benefits may be achieved. These and other benefits will be described in more throughout the present specification and more particularly below.

Various additional embodiments, features and advantages of the present invention can be more fully appreciated with reference to the detailed description and accompanying drawings that follow.

DETAILED DESCRIPTION OF THE INVENTION

Embodiments of the present invention provide techniques for processing integrated circuits for the manufacture of semiconductor devices. In particularly, embodiments of the invention provide a method and system for performing patterning processes for the manufacture of integrated circuit devices. More particularly, the present method provides an image capturing and processing technique for identifying repeating pattern defects in a retical mask used for the manufacture of integrated circuits. But it would be recognized that the invention has a much broader range of applicability. As merely an example, the method and system can be applied to other devices such as micro electrical mechanical systems, display devices, and others.

Figure 1B:
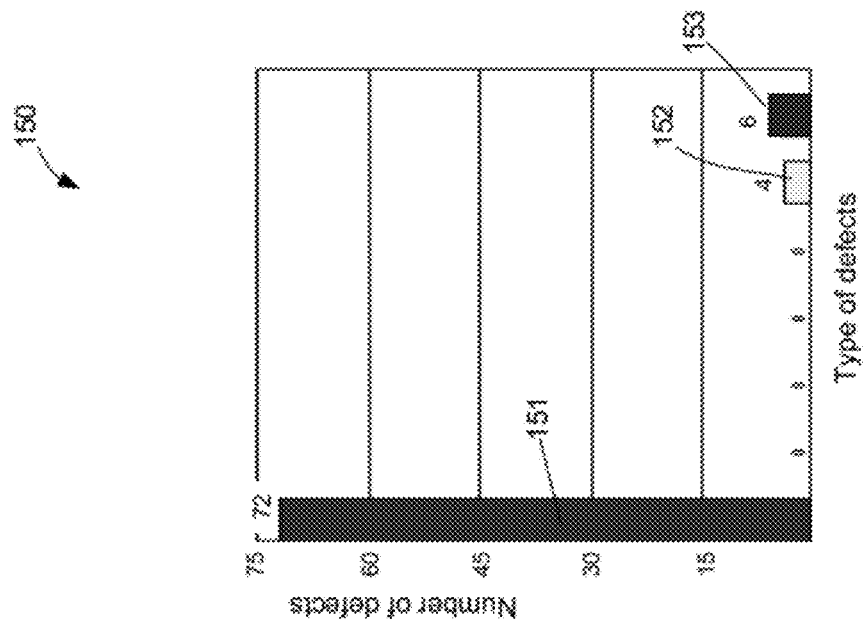
FIG. 1A and FIG. 1B are simplified diagrams illustrating a top-view of a partially completed wafer and associated defect information.
Figure 1A:
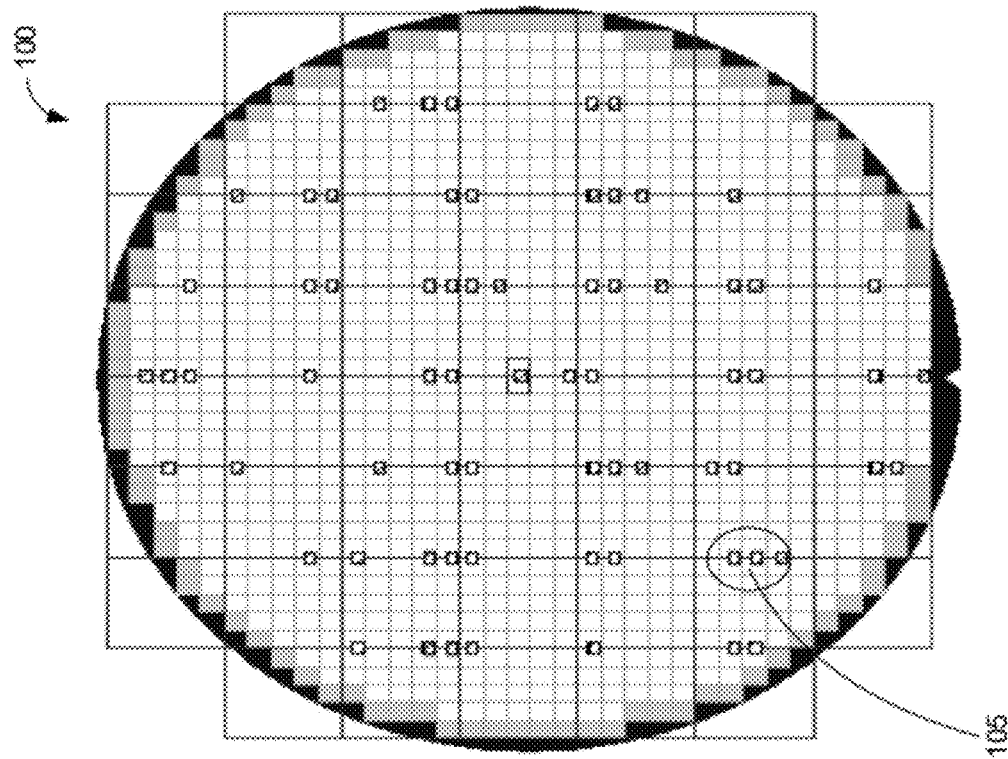

As background information, we have discovered that reticle defects in lithography are problematic. That is, as more PSM (phase shift mask) reticles are implemented into lithography for critical fabrication processes of 100 nm node technology and beyond to enlarge the lithography process window, automatic identification and quick response to lithographic reticle defects have become more important. This issue is often more pronounced with advanced technology. Any reticle defect, commonly called repeating defect, could damage an integrated circuit. As an example, using a reticle having an array size of two by three, a defect on any array portion can lead to a repeating defect totaling ⅙ of the total dies on the in-process wafer. As merely an example, FIG. 1A illustrates a simplified diagram illustrating a top-view of a partially processed wafer 100 and FIG. 1B illustrates the associated defect information 150. As shown, the partially processed wafer includes a plurality of dies. The top view diagram of the partially processed wafer illustrates a number of repeating defects 105 that span over the plurality of dies. FIG. 1B shows the number of defects as a function of the defect types. For example, defects 151 can be associated as repeating defects types 153 of defect according to a specific embodiment. A repeating defect 151 is illustrated. In some applications, the defect can be repaired. As an example for memory products, a repeating defect located in a cell area is often repairable. Unfortunately, additional defects that can be repeatable or combined with other types of defects, can give rise to higher yield loss.

Figure 2:
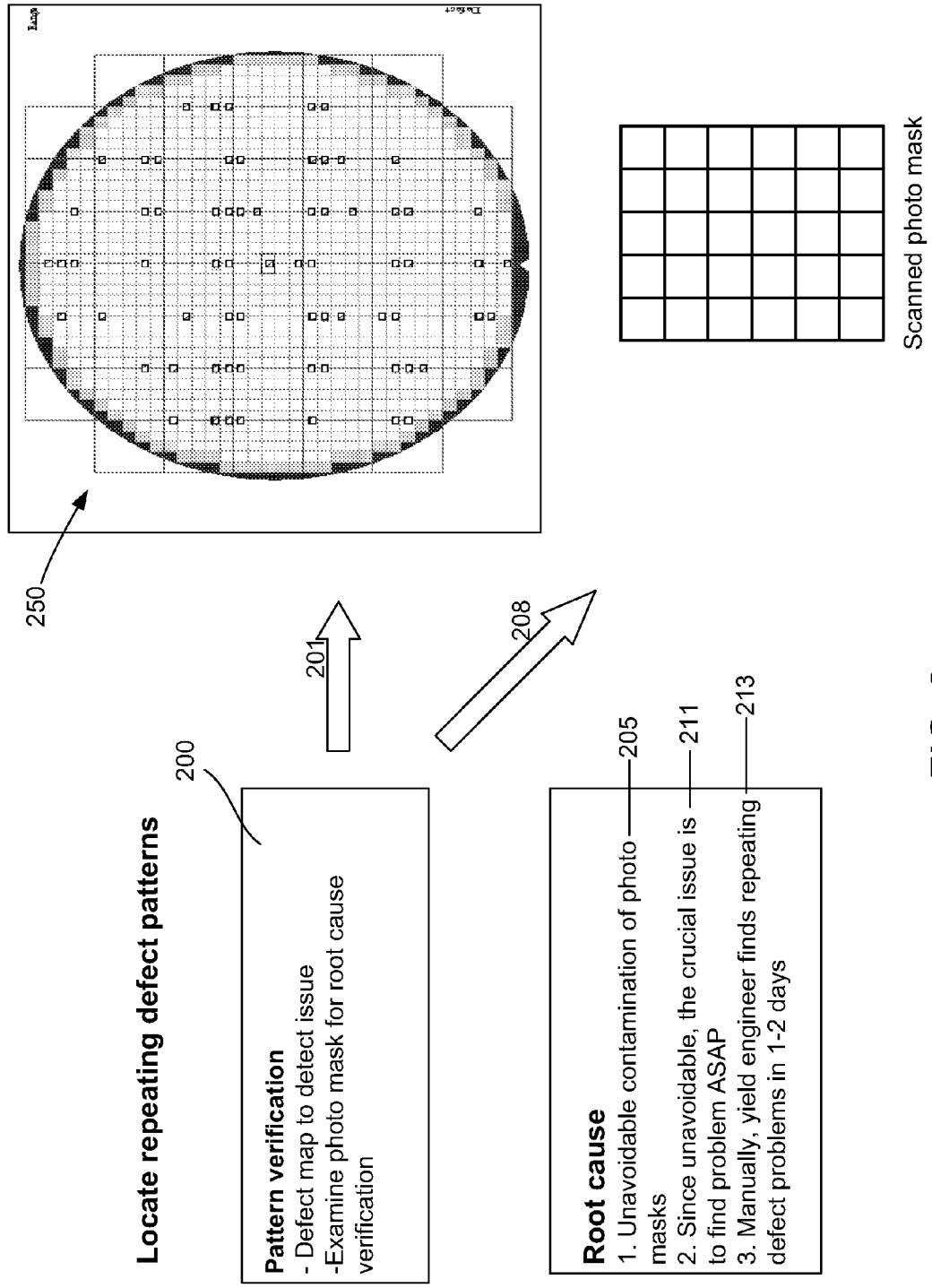
FIG. 2 illustrates a process for detecting a repeating defect on a reticle.

In many if not substantially all cases, repeating defects are often unavoidable 205, as illustrated by FIG. 2. As shown, defects are identified on wafer 250 during a first step 201. Once the wafer is identified, the defects are traced back to a reticle 208 according to a specific embodiment. Lithographic masks often become contaminated with particulates during and throughout the manufacturing process. Although we can often reduce the damage caused by repeating defects, the repeating defects cannot be completely eliminated during the manufacture of the integrated circuits. We have discovered that it is important to respond promptly (211) to identify and resolve the issue of repeating defects. Here, we must often quickly identify emerging repeating defect excursions, stop the relevant process step in the process line, clean the defective reticle, and minimize the impacted lots. To capture this repeating defect issue, yield engineers (213) often manually and visually examined the defect wafer maps and determined if and when repeating defects had occurred. This manual and visual process is often tedious and typically results in delayed detection or completely misses the detection of the defective reticle.

Figure 3:
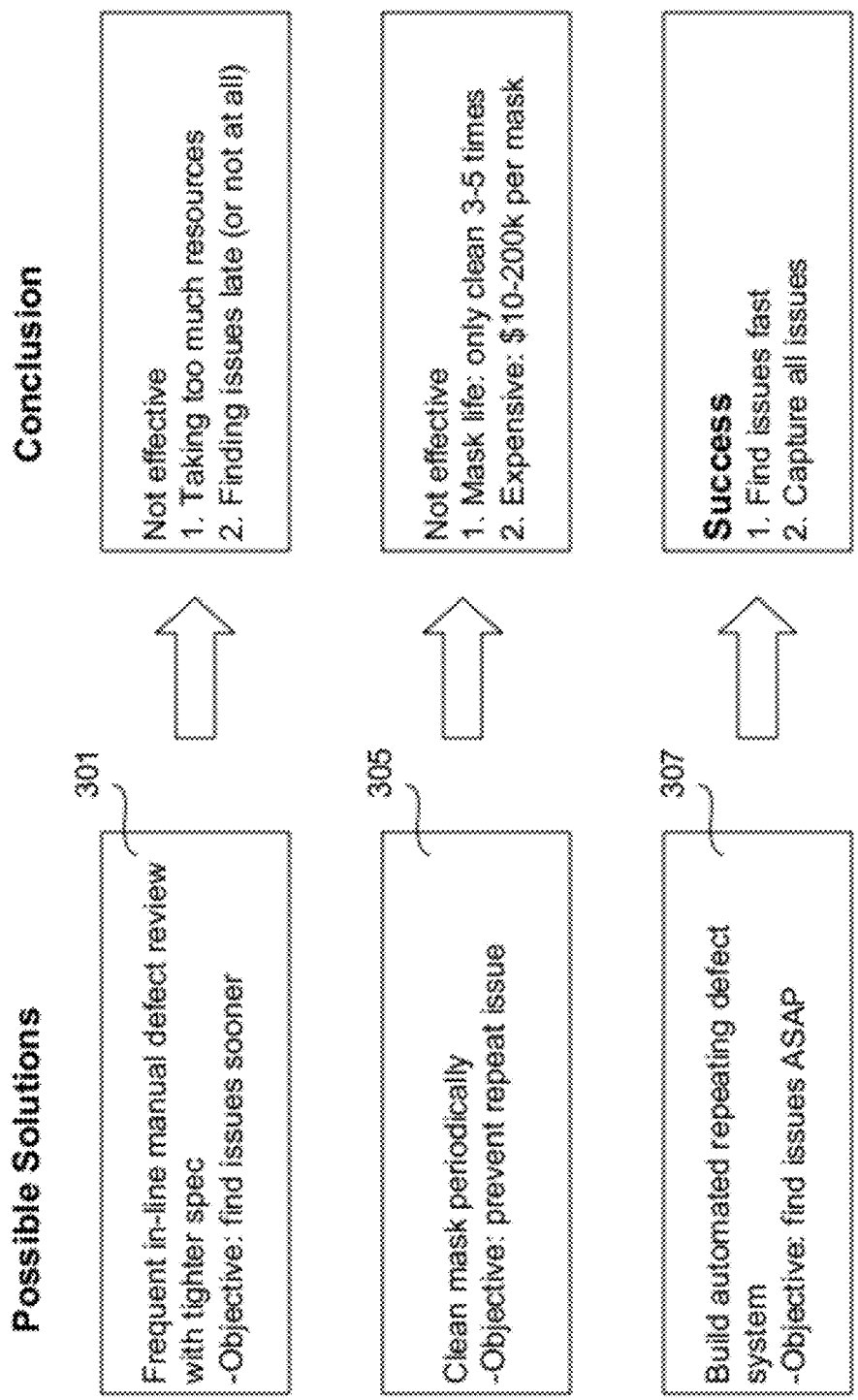
FIG. 3 is a simplified diagram illustrating alternative solutions for identifying a repeating defect according to an embodiment of the present invention.

To effectively solve the repeating defect issue, we developed an automatic repeating defect detection system according to an embodiment of the present invention. FIG. 3 is a simplified diagram illustrating a process for identifying a repeating defect according to an embodiment of the present invention. This diagram is merely an example, which should not unduly limit the scope of the claims herein. One of ordinary skill in the art would recognize many variations, modifications, and alternatives. As shown, we identified several possible solution: one of the possible solutions is a frequent in-line manual defect review (301); another possible solution is to clean the mask periodically (305); and yet another possible solution is an embodiment of the present invention (307). As shown, the solutions (301), (305) are generally not effective and/or not feasible due to costs. In a specific embodiment, the present invention provides a system which includes statistical analysis to automate the identification of scanned defect wafer for repeated defects in real-time. The novel statistical analysis process reduces the amount of analysis performed by engineers and, more importantly, reduces the time to identify the reticle defect problem. The system according to an embodiment of the present invention performed successfully. The system had stopped the operation upon identifying repeating defects caused by defective reticles.

In a specific embodiment, a method for processing an integrated circuit device is outlined below.

1. Provide a partially completed semiconductor wafer, which has one or more patterns;

2. Capture an image of the pattern using one or more scans across a surface of the partially completed wafer;

3. Transform information associated with the image of the pattern in a first format (e.g., a pixel domain) into a second format, e.g., a transform domain;

4. Determine defect information associated with the image of the pattern in the second format;

5. Process the defect information of the partially completed wafer to identify at least one defect associated with a spatial location of a repeating pattern on the partially processed wafer provided by a reticle;

6. Identify the reticle associated with the defect and a stepper associated with the reticle having the defect;

7. Cease operation of the stepper with the defective reticle;

8. Replace the damaged reticle with a second reticle on the stepper;

9. Resume operation of the stepper with the second reticle, which is free from defects; and 10. Perform other steps as desired.

The above sequence of steps provides a method according to an embodiment of the present invention. As shown, the method uses a combination of steps including a way of identifying repeating defects in the manufacture of integrated circuits according to an embodiment of the present invention. Other alternatives can also be provided where steps are added, one or more steps are removed, or one or more steps are provided in a different sequence without departing from the scope of the claims herein. Details of the present method and structure can be found throughout the present specification and more particularly below.

Figure 4:
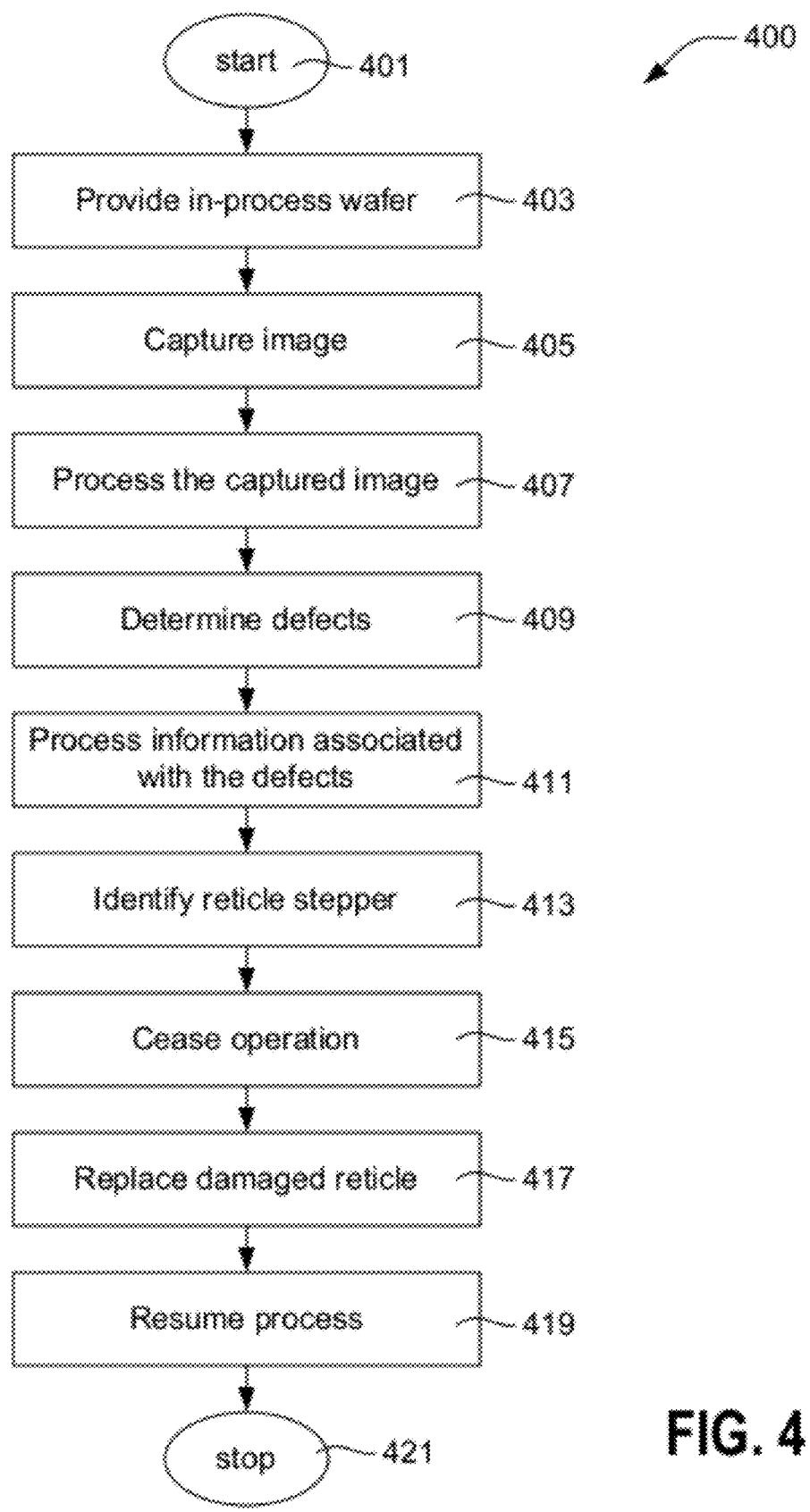
FIG. 4 is a simplified flow diagram illustrating a method for identifying a repeating defect according to an embodiment of the present invention.

FIG. 4 is a simplified flow diagram 400 illustrating a method for identifying a repeating defect according to an embodiment of the present invention. This diagram is merely an example, which should not unduly limit the scope of the claims recited herein. One of ordinary skill in the art would recognize other variations, modifications, and alternatives. In a specific embodiment, the present invention provides a method for processing an integrated circuit device, e.g., memory, application specific integrated circuits, microprocessors, and others. The method begins at start (step 401). The method includes providing a partially completed semiconductor wafer (step 403), which has one or more patterns. In a specific embodiment, the partially completed wafer can be provided after any patterning process (e.g., metal patterns, dielectric patterns, STI patterns, gate patterns) and/or other suitable step. Of course, there can be other variations, modifications, and alternatives.

In a specific embodiment, the method includes capturing (step 405) an image of the pattern using one or more scans across a surface of the partially completed wafer. In a specific embodiment, the method uses an imaging device such as a digital camera, scanner, etc. As merely an example, the method can use an inspection tool such as those available from KLA-Tencor Corporation (located at 160 Rio Robles, San Jose, Calif. 95134-1813), but can be from other companies. Of course, there can be other variations, modifications, and alternatives.

The method includes processing information (step 407) associated with the image of the pattern in a first format (e.g., pixel domain) into a second format, e.g., a transform domain, according to a specific embodiment. The method includes determining defect information (step 409) associated with the image of the pattern in the second format. In a specific embodiment, the determining can count the number of defects and/or identify information associated with the defects. Information can include, among others size, location, and other suitable characteristics about the defects such as defect types (single-type defects, group or cluster-type defects, scratch-type, etc.). Of course, there can be other variations, modifications, and alternatives.

In a specific embodiment, the method includes processing (step 411) the defect information of the partially completed wafer to identify at least one defect associated with a spatial location of a repeating pattern on the partially completed wafer provided by a reticle. Depending upon the embodiment, there can be one or more ways to process the information. As merely an example, the processing can use a clustering process, such as the one describe below. Of course, there can be other variations, modifications, and alternatives.

In a preferred embodiment, the method also identifies (step 413) the reticle associated with the defect and a stepper associated with the reticle having the defect. In a specific embodiment, the reticle forms at least four repeating patterns, but may also be a lot more, e.g., 3 by 3, 4 by 4. In a specific embodiment, the reticle is identified by examining the step being patterned, wafer tracking number, and associated process steps used by the wafer. In a specific embodiment, the method ceases (step 415) operation of the stepper within a predetermined time of identifying the defective reticle. In a preferred embodiment, the stepper with a damaged reticle is ceased before damaging other in-process wafers. In a specific embodiment, the damage may be caused by a crack, contamination, growth, and/or other imperfections, and the like. The damaged reticle is replaced (step 417) or the damaged reticle can be cleaned, and the process resumes (step 419) using a replaced reticle or a clean reticle, which is free from defects according to a specific embodiment. As shown, the method stops, at step 421. Of course, there can be other variations, modifications, and alternatives.

Figure 5:
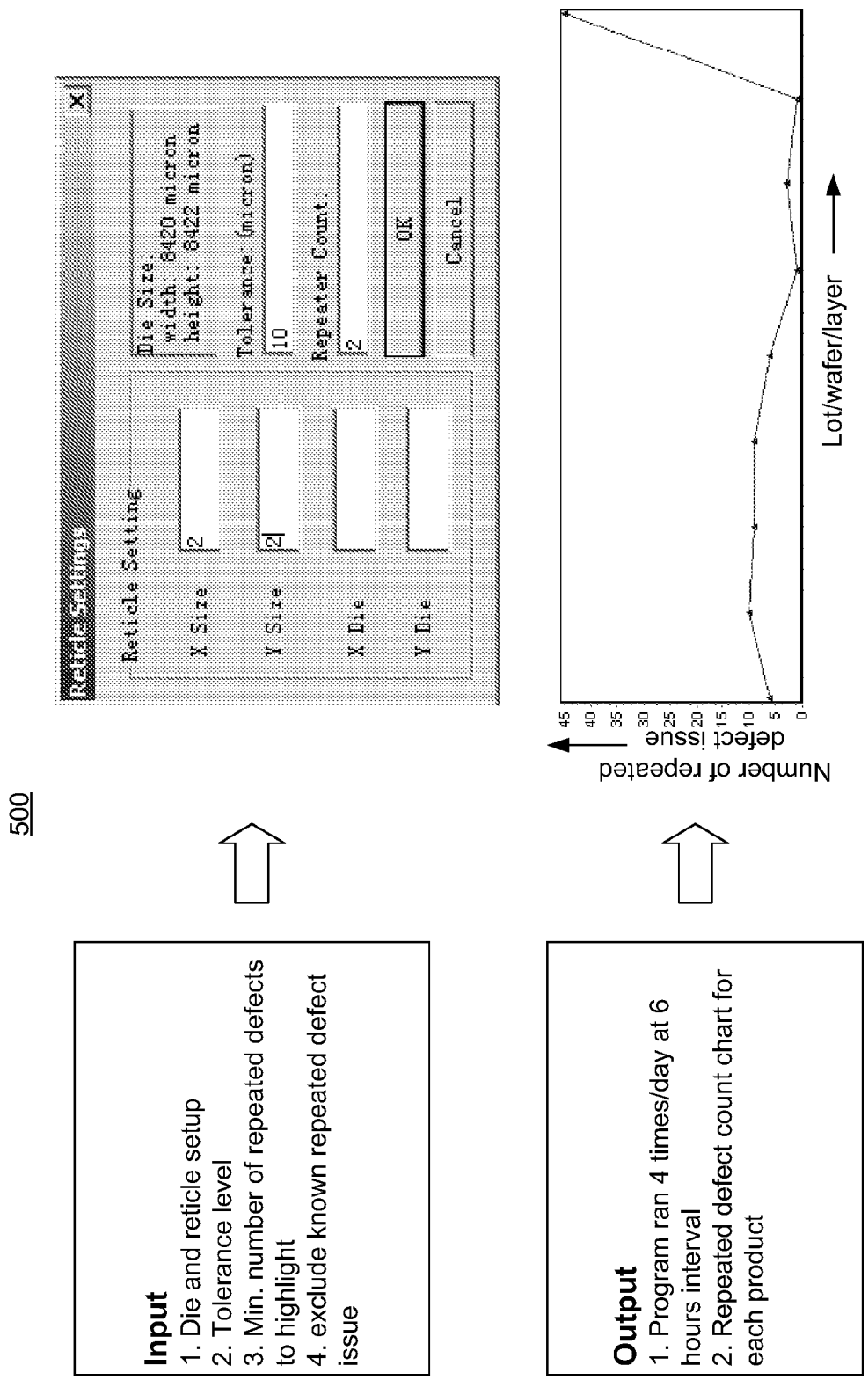
FIG. 5 is a simplified diagram illustrating input/output information for a system according to an embodiment of the present invention.

FIG. 5 is a simplified diagram illustrating input/output information for a system 500 according to an embodiment of the present invention. This diagram is merely an example, which should not unduly limit the scope of the claims recited herein. One of ordinary skill in the art would recognize other variations, modifications, and alternatives. In an embodiment, the system, which is computer based, includes input information 1, 2, 3, 4. The system also has output information 1 and 2. The plot illustrates repeated defect count (on the y-axis) against lot/wafer/layer information on the x-axis. Of course, there can be other variations, modifications, and alternatives. Further details of the present system can be found throughout the present specification and more particularly below.

In a specific embodiment, the invention provides an automated repeating defect detection system 600 for processing an integrated circuit device. The system 600 includes a wafer inspection apparatus 610 configured to inspect partially completed wafers. The wafer inspection apparatus may include an optical scanner, a scanning electron microscope (SEM), or a high resolution digital camera. As merely an example, the inspection apparatus may be an inspection tool available from KLA-Tencor Corporation. The automated repeating defect detection system also includes a processing unit 620 configured to determine the types, location and other characteristics of defects. In addition, the system 600 includes a memory unit 630 containing program codes associated with the operation of the processing unit. In an embodiment, the memory unit, which can be a RAM, DRAM, disk storage, flash device, and the like, includes a database for storing defect information such as types, location of the defects, and/or wafer IDs, etc. The memory unit may include various computer program codes to instruct the processing unit to process the defect information of a partially completed wafer and to identify at least one defect associated with a spatial location of a repeating pattern on the partially completed wafer provided by a reticle. In a specific embodiment, the computer codes are designed to automatically process defect information in a first format and identify at least one defect associated with a spatial repeating pattern on a reticle automatically.

In an embodiment, the program codes include an analysis process to automate the identification of reticle repeating defects to allow efficient identification of mask defects. An overall analysis process may include the following:

1. Use agglomerative hierarchical clustering with farthest neighbor distance metric to identify defects in the same dies that are within the tolerance level and define a virtual defect at the center of these defects.

2. Overlay dies with the same reticle position and use hierarchical clustering with average distance metric to identify defects across different dies in the same reticle position that are within the tolerance level.

3. Defects that are in the same cluster are systematic repeating defects across the reticle and are likely caused by mask defects at the relevant lithography process steps.

4. Once yield engineers identified the source of a particular reticle repeating defect pattern, yield engineers may ignore the same reticle repeating defect data in subsequent wafers and concentrate on new repeating defect data or other yet unidentified issues.

5. The analysis may remove the same reticle repeating defect data in subsequent wafers in the identified locations and classify them into a separate "known repeated defect" bin.

6. Using cluster analysis to identify repeated reticle defects on wafers. We may substitute different distance metrics, different clustering or classification methods (k-mean, model-based clustering, etc.). We can also use this analysis process to find repeating defects that are caused by imperfect processes or design rule violation rather than caused by damaged or defective reticle according to a specific embodiment.

Figure 6A:
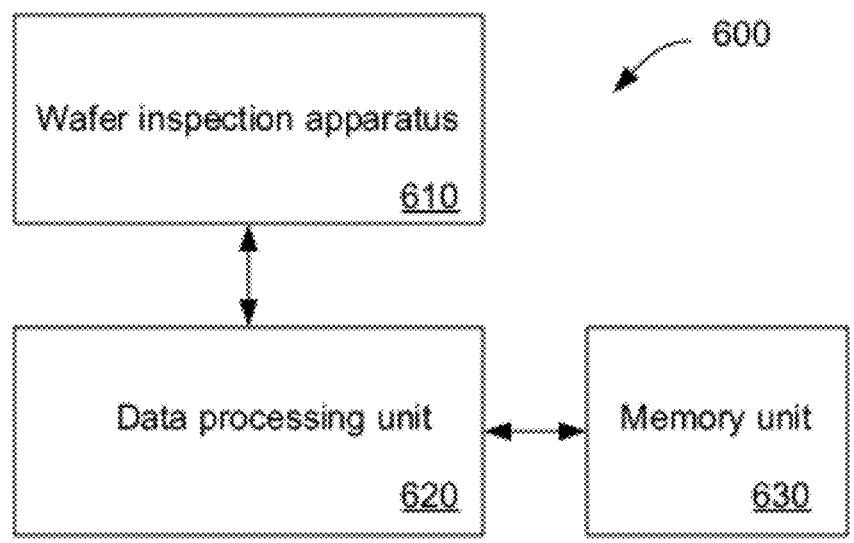
FIG. 6A is a simplified block diagram of an automated repeating defect detection system 600 for processing an integrated circuit device according to an embodiment of the present invention.
Figure 6B:
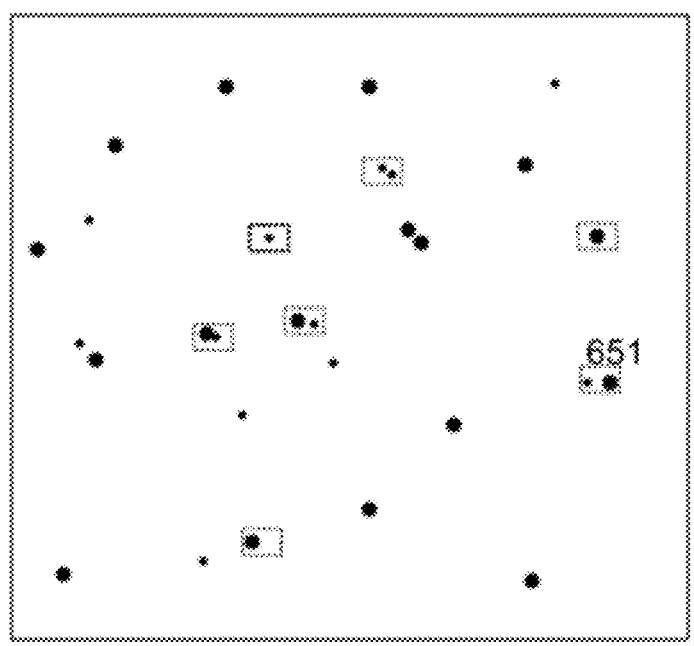
FIG. 6B is an example of clusters of defects according to embodiments of the present invention.

According to some embodiments, several well-known defect clustering algorithms such as Odyssey DDMS (Defect Data Management System), hierarchical clustering, discriminant analysis, K-mean, model-based, etc. may be used. FIG. 6B shows a hierarchical clustering algorithm.

1. Initially, each defect is assigned to its own cluster and then the algorithm iteratively join clusters that are closest to each other into a combined cluster. This procedure continues until all defects are assigned into a single cluster. As shown in FIG. 6B, each defect 601 starts as its own cluster according to a specific embodiment.

Figure 7:
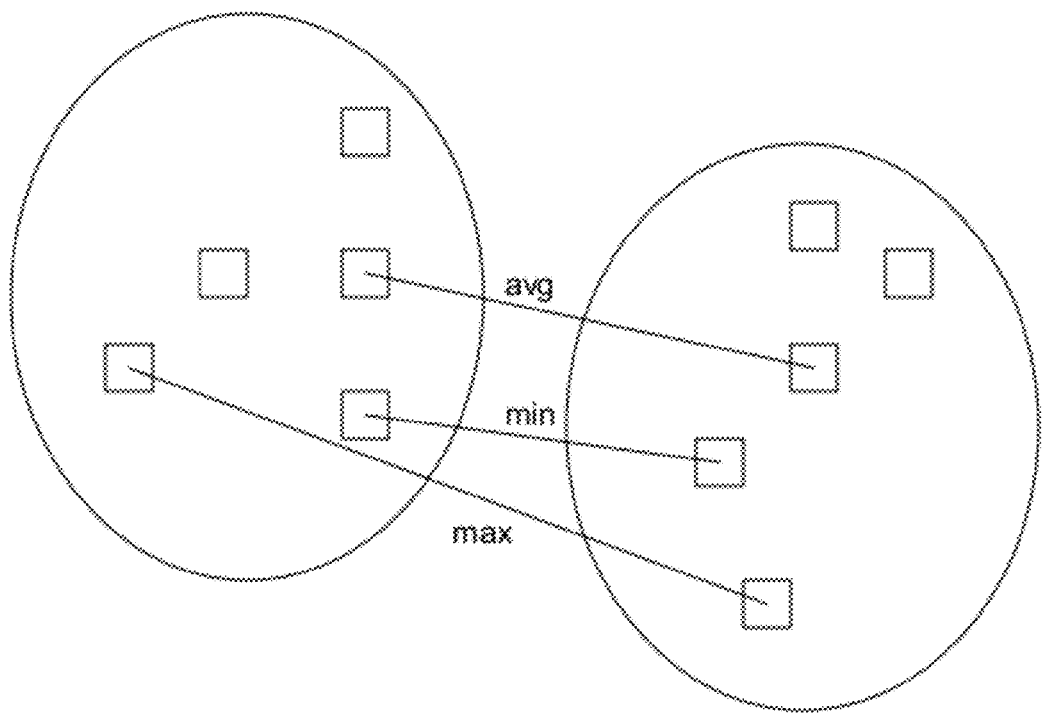
FIG. 7 is a simplified diagram illustrating a distance metric according to an embodiment of the present invention.

2. Euclidean distance is used to compute the distance between any two defects. For defects clusters, distance metrics will be used, as illustrated in FIG. 7 according to an embodiment of the present invention. This diagram is merely an example, which should not unduly limit the scope of the claims recited herein. One of ordinary skill in the art would recognize other variations, modifications, and alternatives. There are several ways to define distances between clusters.

a) Farthest neighbor, complete linkage method: the distance between 2 clusters is the farthest distance between some defects from one cluster to the other $$d_{max}(D_i, D_j) = \max_{x \in D_i, y \in D_j} \|x - y\|$$

b) Nearest neighbor, single linkage method: the distance between 2 clusters is the shortest distance between some defects from one cluster to the other $$d_{min}(D_i, D_j) = \min_{x \in D_i, y \in D_j} \|x - y\|$$

c) Average distance method: average of the distance pairs between two clusters $$d_{avg}(D_i, D_j) = \frac{1}{n_i n_j} \sum_{x \in D_i} \sum_{y \in D_j} \|x - y\|$$

Figure 8:
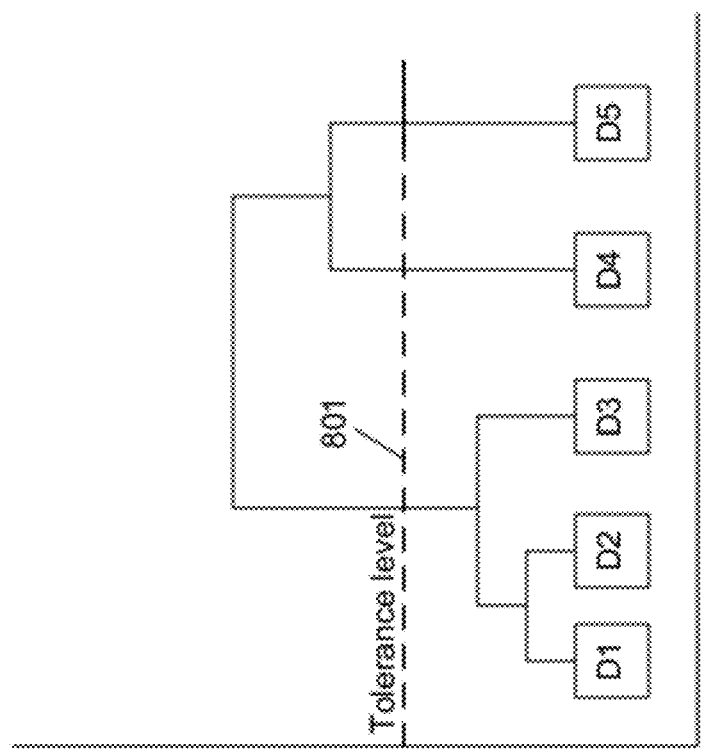
FIG. 8 is a simplified diagram illustrating a clustering method according to an embodiment of the present invention.
Figure 8:
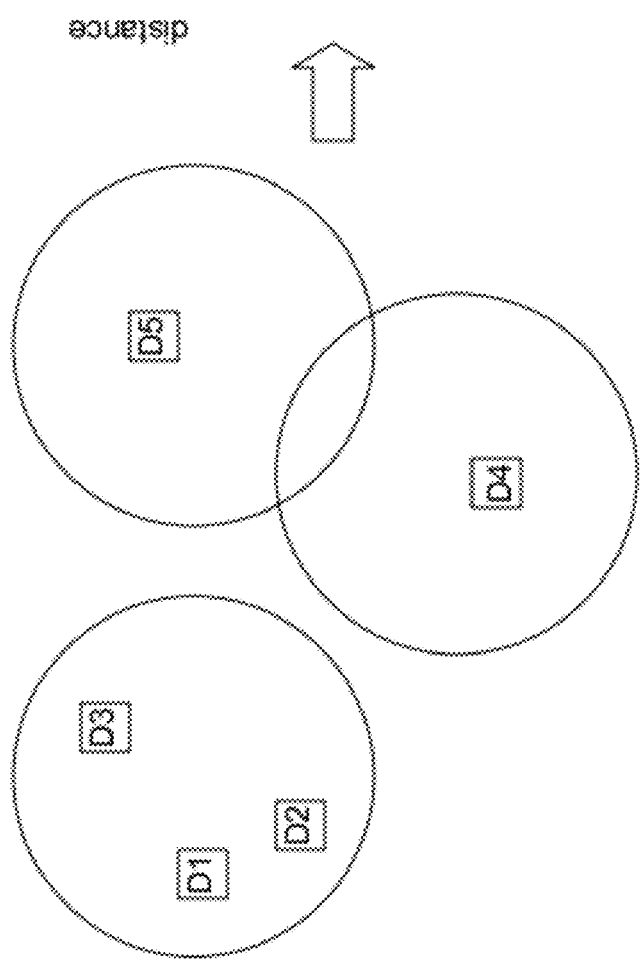

The size of a cluster of defect is the largest distance of the defects in this cluster with the defined distance metrics above according to a specific embodiment. So the given tolerance level is used as a cutoff to identify defects that are in clusters smaller than this specified tolerance distance. See for example, FIG. 8, which is a simplified diagram illustrating a clustering method according to an embodiment of the present invention. This diagram is merely an example, which should not unduly limit the scope of the claims recited herein. One of ordinary skill in the art would recognize other variations, modifications, and alternatives. As shown, tolerance level 801 is identified which is used as a cut off to identify defects that are in clusters D1, D2, D3, D4, and D5. Of course, there can be other variations, modifications, and alternatives.

The above sequence of steps provides a method according to an embodiment of the present invention. As shown, the method uses a combination of steps including a way of identifying repeating defects in the manufacture of integrated circuits according to an embodiment of the present invention. Other alternatives can also be provided where steps are added, one or more steps are removed, or one or more steps are provided in a different sequence without departing from the scope of the claims herein. Details of the present method and structure can be found throughout the present specification and more particularly below.

It is also understood that the examples and embodiments described herein are for illustrative purposes only and that various modifications or changes in light thereof will be suggested to persons skilled in the art and are to be included within the spirit and purview of this application and scope of the appended claims. Further details of certain experimental results of the present method and system can be found throughout the present specification and more particularly below.

Examples

To prove the operation and effectiveness of the present invention, we performed certain experiments. These experiments are merely examples, which should not unduly limit the scope of the claims herein. One of ordinary skill in the art would recognize many other variations, modifications, and alternatives. Further details of the present method and system can be found throughout the present specification and more particularly below.

In a specific embodiment, we achieved certain benefits using the present method and system. As an example, the response time was reduced from 24-48 hours to 12-24 hours in the present implementation (i.e., analysis ran on the database data on set number of times per day). Once the present method and system are provided using a real-time system, the detection time will be further reduce to 6-12 hours (e.g., essentially just the elapsed time between process stop and defect scan step) according to a preferred embodiment.

Not only does this repeating defect detection system reduce the detection time, it also saves lots of engineering effort in identifying and classifying the repeating defect occurrences according to a specific embodiment. This implies that we currently save about ½ lots from the repeating defect impact and we can look forward to improve the impact rate to about ¼ of the current rate with the real-time system. Of course, there can be other variations, modifications, and alternatives.

In one case, one reticle mask repeating excursion impacted 36 lots before detected manually. After implementing the current repeating detect system, the impact lots would be reduced to less than 20 lots. When we implement the real-time detection system, the impact will be improved to less than 10 lots. With a conservative estimation that this repeating defect resulted in a 10% yield loss at the average cost of $1000 USD, the current detection system could save $40,000 USD. With the real time detection system, saving up to $65,000 USD can be achieved. In addition, if wafers need to be scrapped as a result of repeating defects, the savings would be even greater.

Conservatively, we estimated that repeating defect excursion occurs 20-30 times per year per fab with various impact levels. These 20-30 repeating defect excursions could be reduced by other preventive measures. But as we discussed earlier, they are unavoidable. Out of the 20-30 repeating defective excursions, we estimate that we can save, on an average 10 lots per excursion or 200-300 lots per year per wafer fabrication facility by implementing the real-time detection system. Of course there can be other variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for processing an integrated circuit device, the method comprising:
   providing a partially completed semiconductor wafer, the partially completed semiconductor wafer including one or more patterns;
   capturing an image of the one or more patterns using one or more scans across a surface of the partially completed wafer;
   processing information associated with the image of the one or more patterns in a first format into a second format;
   determining defect information associated with the image of the one or more patterns in the second format;
   processing using a clustering process the defect information of the partially completed wafer to identify at least one defect associated with a spatial location of a repeating pattern on the partially completed wafer provided by a reticle;
   identifying the reticle associated with the at least one defect and a stepper associated with the reticle having the at least one defect; and
   ceasing operation of the stepper.

2. The method of claim 1 wherein the defect information provides data in a format of wafer identification, product identification, layer information, and x-y die scanned.

3. The method of claim 1 wherein the defect information comprises a number of defects.

4. The method of claim 1 wherein the defect information comprises a die identification, a location of defect on the die, and a type of defect.

5. The method of claim 1 wherein the repeating pattern on the reticle comprises at least four of the repeating patterns.

6. The method of claim 1 wherein the one or more patterns on the partially completed wafer are associated with one or more metal patterns.

7. The method of claim 1 wherein the one or more patterns on the partially completed wafer are associated with one or more STI patterns.

8. The method of claim 1 wherein the one or more patterns on the partially completed wafer are associated with one or more dielectric patterns.

9. The method of claim 1 wherein the one or more patterns on the partially completed wafer are associated with one or more gate patterns.

10. The method of claim 1 wherein the clustering process comprises a hierarchical clustering process.

11. The method of claim 10 wherein the hierarchical clustering process is a hierarchical agglomerative clustering process.

12. The method of claim 1 wherein the at least one defect is associated with a particle.

13. The method of claim 1 wherein the at least one defect is associated with a crack in the reticle.

14. The method of claim 1 wherein the at least one defect is associated with a growth provided on a portion of the reticle.

15. The method of claim 1 wherein the determining defect information associated with the image of the pattern in the second format and the processing the defect information of the partially completed wafer to identify at least one defect associated with a spatial location of a repeating pattern on a reticle are performed automatically.

16. The method of claim 1 further comprising outputting the at least one defect in visual form.

17. The method of claim 1 wherein the at least one defect is associated with a plurality of repeating defects.

18. A system for processing an integrated circuit device, the system comprising:
   an image capturing unit configured to capture an image of a partially completed wafer;
   a processor unit configured to convert information associated with the captured image into a transform domain; and
   a memory unit coupled to the processor unit, the memory unit comprising:
      one or more program codes configured to determine defect information associated with the captured image in the transform domain;
      one or more program codes configured to process the defect information using a clustering analysis to identify at least one defect associated with a spatial location of a repeating pattern provided by a reticle on the partially completed wafer; and
      one or more codes configured to identify the reticle associated with the at least one defect.

19. The system of claim 18 wherein the clustering analysis comprises a hierarchical clustering process.

20. The system of claim 19 wherein the hierarchical clustering process is an agglomerative clustering process.

* * * * *